United States Patent
Zhang et al.

(10) Patent No.: US 8,324,433 B2
(45) Date of Patent: Dec. 4, 2012

(54) METHOD FOR PRODUCING ETHYLENE GLYCOL FROM POLYHYDROXY COMPOUND

(75) Inventors: Tao Zhang, Dalian (CN); Mingyuan Zheng, Dalian (CN); Aiqin Wang, Dalian (CN); Na Ji, Dalian (CN); Jifeng Pang, Dalian (CN); Zhijun Tai, Dalian (CN); Likun Zhou, Dalian (CN); Jingguang Chen, Dalian (CN); Xiaodong Wang, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 12/916,625

(22) Filed: Oct. 31, 2010

(65) Prior Publication Data
US 2011/0046419 A1    Feb. 24, 2011

Related U.S. Application Data

(63) Continuation of application No. PCT/CN2009/074821, filed on Nov. 5, 2009.

(30) Foreign Application Priority Data

Nov. 26, 2008    (CN) .......................... 2008 1 0229065

(51) Int. Cl.
*C07C 29/132*    (2006.01)
*C07C 29/60*    (2006.01)

(52) U.S. Cl. ...................................................... 568/861
(58) Field of Classification Search .................... 568/861
See application file for complete search history.

(56) References Cited

FOREIGN PATENT DOCUMENTS
IN    194851    * 12/2004

OTHER PUBLICATIONS

Vidyarthi, English abstract only of Indian Patent IN-194851.*

* cited by examiner

*Primary Examiner* — Elvis O Price
(74) *Attorney, Agent, or Firm* — Matthias Scholl P.C.; Matthias Scholl

(57) ABSTRACT

A method for producing ethylene glycol, including (a) adding a polyhydroxy compound and water to a sealed high-pressure reactor, (b) removing air and introducing hydrogen, and (c) allowing the polyhydroxy compound to react in the presence of a catalyst while stiffing. The catalyst includes a first active ingredient and a second active ingredient. The first active ingredient includes a transition metal of Group 8, 9, or 10 selected from iron, cobalt, nickel, ruthenium, rhodium, palladium, iridium, and platinum, and/or a mixture thereof. The second active ingredient includes a metallic state of molybdenum and/or tungsten, or a carbide, nitride, or phosphide thereof. The method is carried out at a hydrogen pressure of 1-12 MPa, at a temperature of 120-300° C. for not less than 5 min in a one-step catalytic reaction. The efficiency, selectivity, and the yield of ethylene glycol are high. The preparation process is simple and the materials used are renewable.

20 Claims, No Drawings

METHOD FOR PRODUCING ETHYLENE GLYCOL FROM POLYHYDROXY COMPOUND

CROSS-REFERENCE TO RELATED APPLICATIONS

This application is a continuation of International Patent Application No. PCT/CN2009/074821 with an international filing date of Nov. 5, 2009, designating the United States, now pending, and further claims priority benefits to Chinese Patent Application No. 200810229065.8 filed Nov. 26, 2008. The contents of all of the aforementioned applications, including any intervening amendments thereto, are incorporated herein by reference.

BACKGROUND OF THE INVENTION

1. Field of the Invention

The invention relates to a method for producing ethylene glycol, and more particularly to a method for producing ethylene glycol from a polyhydroxy compound under hydrothermal conditions.

2. Description of the Related Art

Conventional methods for producing ethylene glycol involve oil as raw material. For example, ethylene is epoxidized to yield ethylene oxide which is hydrated to yield ethylene glycol. Oil is a non-renewable resource and these methods include a step of selective oxidization or epoxidation, which increases the technical difficulty of the process. Furthermore, conventional methods have low efficiency and high material consumption, can produce serious pollution, and produce a large quantity of by-products.

Producing ethylene glycol with renewable raw materials can reduce human dependence on fossil materials and is conducive to achieving sustainable development in terms of both the environment and the economy.

Polyhydroxy compounds, such as starch, hemicellulose, glucose, sucrose, fructose, and fructan, are very common in nature and the yields thereof are on the increase with the development of agricultural technologies. Producing ethylene glycol using polyhydroxy compounds not only reduces human dependence on fossil materials but also improves the added value of agricultural products.

Conventional methods for producing ethylene glycol from polyhydroxy compounds include the steps of: (a) gelatinizing, liquefying, and saccharifying starch to yield glucose; (b) hydrotreating the glucose with ruthenium or nickel as catalyst to yield sorbitol; and (c) degrading the sorbitol by hydrogenolysis under high temperature and high pressure conditions to yield a mixture that mainly includes propylene glycol, glycerol, and ethylene glycol. The yields of ethylene glycol are between 10% and 30% and the preparation methods are complex.

SUMMARY OF THE INVENTION

In view of the above-described problems, it is one objective of the invention to provide a method for producing ethylene glycol from a polyhydroxy compound in high yield and with high selectivity. The polyhydroxy compound, including but not limited to starch, hemicellulose, glucose, sucrose, fructose, and fructan, is degraded via one-step catalytic hydrogenation to yield ethylene glycol.

To achieve the above objective, in accordance with one embodiment of the invention, there is provided a method for producing ethylene glycol, the method comprising:(a) adding a polyhydroxy compound and water to a sealed high-pressure reactor, (b) charging the reactor with hydrogen, and (c) allowing the polyhydroxy compound to react in the presence of a catalyst while stirring the reaction mixture; the catalyst comprising a first active ingredient and a second active ingredient, the first active ingredient comprising a transition metal of Groups 8, 9, or 10(standard period table, IUPAC system) selected from iron, cobalt, nickel, ruthenium, rhodium, palladium, iridium, and platinum, or a mixture thereof; the second active ingredient comprising a metallic state of molybdenum and/or tungsten, or a carbide, nitride, or phosphide thereof; an initial hydrogen pressure therein at room temperature being between 1 and 12 MPa, the reaction temperature being between 120 and 300° C., and the reaction time being not less than 5 min.

In a class of this embodiment, the polyhydroxy compound is a starch, hemicellulose, glucose, sucrose, fructose, or fructan.

In a class of this embodiment, the initial hydrogen pressure in the reactor at room temperature is between 3 and 7 MPa, the reaction temperature is between 180 and 250° C., and the reaction time is between 30 and 180 min.

In a class of this embodiment, the weight ratio of the second active ingredient to the first ingredient is between 0.02 and 1600, and particularly between 0.3 and 60.

In a class of this embodiment, the first and second active ingredient are carried by a carrier comprising activated carbon, alumina, silica, silicon carbide, zirconia, zinc oxide, titanium dioxide, and/or a mixture thereof.

In a class of this embodiment, the metal component of the first active ingredient accounts for between 0.05 and 50 wt % of the catalyst, and particularly between 1 and 30 wt %.

In a class of this embodiment, the metal component of the second active ingredient accounts for between 1 and 80 wt % of the catalyst, and particularly between 10 and 60 wt %.

In a class of this embodiment, the catalyst is not supported and an active ingredient thereof functions as a skeletal catalyst, for example, a Raney nickel.

In a class of this embodiment, the weight ratio of the polyhydroxy compound to water is between 1:200 and 1:4.

In a class of this embodiment, the weight ratio of the polyhydroxy compound to the catalyst is between 1:1 and 100:1.

In a class of this embodiment, the high-pressure reactor is substituted with an optimized reactor, for example, a fixed bed reactor or a slurry bed reactor, so that the mass transfer and reaction between the polyhydroxy compound, hydrogen, and catalyst are optimal.

Advantages of the invention are summarized below:
1) The invention uses renewable polyhydroxy compounds, e.g., starch, hemicellulose, glucose, sucrose, fructose, or fructan as the raw material, thereby satisfying the requirement of sustainable development;
2) The carbon, hydrogen, and oxygen atoms of the raw materials are retained in the degradation products of the polyhydroxy compounds to a large degree, which means that the preparation method has a high atom economy;
3) Compared with conventional methods for producing ethylene glycol, the method of the invention involves no sorbitol, and ethylene glycol is produced via one step reaction only; thus, the method is simple and easily implemented on an industrial scale; and
4) The method of the invention yields products in high yield and high selectivity; the yield of ethylene glycol exceeds 50%; and the invention shows great economic and social promise.

DETAILED DESCRIPTION OF THE EMBODIMENTS

For further illustrating the invention, experiments detailing a method for producing ethylene glycol from a polyhydroxy compound are described below. It should be noted that the following examples are intended to describe and not to limit the invention.

EXAMPLE 1

Preparation of a Tungsten Catalyst

Anactive carbon (AC) carrier was soaked with 0.4 g/mL ammonium metatungstate solution. The mixture was dried in an oven at 120° C. for 12 hrs and reduced in the presence of hydrogen at 700° C. for one hour to yield a W/AC catalyst comprising 20 wt % of tungsten.

EXAMPLE 2

Preparation of a Nickel-Tungsten Catalyst

The W/AC catalyst obtained as described in Example 1 was further soaked in a nickel nitrate solution, dried at 120° C., and reduced at 400° C. for 2 hrs to yield a Ni—W/AC catalyst comprising 5 wt % of nickel and 18 wt % of tungsten.

EXAMPLE 3

Preparation of Ni/AC, $Ni/SiO_2$, Pt/AC, Ru/AC catalysts

Active carbon carriers were soaked separately in aqueous solutions of nickel nitrate, chloroplatinic acid, and ruthenium trichloride. The mixtures were dried at 120° C. for 12 hrs and reduced in the presence of hydrogen at 450° C. for one hour to yield: a Ni/AC catalyst comprising 5 wt % of nickel, a Pt/AC catalyst comprising 0.5 wt % of platinum, or a Ru/AC catalyst comprising 5 wt % of ruthenium, respectively.

In a separate preparation, active carbon was substituted with $SiO_2$, and following the above steps, a $Ni/SiO_2$ catalyst comprising 15 wt % of nickel was prepared.

EXAMPLE 4

Preparation of a Platinum-Tungsten Catalyst

A carrier of silica was soaked in a 0.2 g/mL ammonium metatungstate solution. The mixture was dried in an oven at 120° C. for 12 hrs and reduced in the presence of hydrogen at 700° C. for one hour to yield a $W/SiO_2$ catalyst comprising 10 wt % of tungsten. The catalyst was further soaked in a chloroplatinic acid solution, dried at 120° C., and reduced in the presence of hydrogenat 350° C. for 2 hrs to yield a Pt—W/$SiO_2$ catalyst comprising 0.5 wt % of platinum and 10 wt % of tungsten.

EXAMPLE 5

Preparation of a Tungsten Carbide Catalyst

A carrier of active carbon was soaked in a 0.4 g/mL ammonium metatungstate solution. The mixture was dried in an oven at 120° C. for 12 hrs and reduced in a carbothermal reaction in the presence of hydrogen at 800° C. for one hour to yield a $W_2C$/AC catalyst comprising 20 wt % of tungsten.

EXAMPLE 6

Preparation of a Nickel-Tungsten Carbide Catalyst

The $W_2C$/AC catalyst prepared according to Example 5 was further soaked in a nickel nitrate solution, dried at 120° C., and reduced at 400° C. for 2 hrs to yield a Ni—$W_2C$/AC catalyst comprising 5 wt % of nickel and 18 wt % of tungsten.

EXAMPLE 7

Preparation of a Ruthenium-Tungsten Carbide Catalyst

A carrier of active carbon was soaked in a mixed solution of ruthenium trichloride and ammonium metatungstate, dried in an oven at 120° C. for 12 hrs, and reduced in a carbothermal reaction in the presence of hydrogen at 700° C. for one hour to yield a Ru—$W_2C$/AC catalyst comprising 5 wt % of ruthenium and 10 wt % of tungsten.

EXAMPLE 8

Preparation of Acobalt-Molybdenum Carbide Catalyst

A carrier of active carbon was soaked in amixed solution of cobalt nitrate and ammonium molybdate with a Mo/Co weight ratio of 2:1, dried in an oven at 120° C. for 12 hrs, and reduced in a carbothermal reaction in the presence of hydrogen at 700° C. for one hour to yield a Co—$Mo_2C$/AC catalyst comprising 10 wt % of cobalt and 20 wt % of molybdenum.

EXAMPLE 9

Preparation of a Tungsten Nitride Catalyst

A carrier of active carbon was soaked in a 0.2 g/mL ammonium metatungstate solution. The mixture was dried in an oven at 120° C. for 12 hrs and nitrided in the presence of $NH_3$ at 700° C. for one hour to yield a $W_2N$/AC catalyst comprising 15 wt % of tungsten.

EXAMPLE 10

Preparation of a Nickel-Tungsten Nitride Catalyst

A mixed solution of ammonium metatungstate and nickel nitrate with a W/Ni weight ratio of 1:1 was prepared and the concentration of ammonium metatungstate was 0.2 g/mL. An active carbon carrier was soaked in the mixture, dried in an oven at 120° C. for 12 hrs, and nitrided in the presence of $NH_3$ at 700° C. for one hour to yield a $N_1$—$W_2N$/AC catalyst comprising 15 wt % of nickel and 15 wt % of tungsten.

EXAMPLE 11

Preparation of a Molybdenum Nitride Catalyst

A carrier of active carbon was soaked in a 0.3 g/mL ammonium molybdate solution. The mixture was dried in an oven at 120° C. for 12 hrs and nitrided in the presence of $NH_3$ at 700° C. for one hour to yield a $Mo_2N$/AC catalyst comprising 25 wt % of molybdenum.

EXAMPLE 12

Preparation of a Nickel-Molybdenum Nitride Catalyst

A mixed solution of ammonium molybdate and nickel nitrate with a Mo/Ni weight ratio of 1:1 was prepared and the concentration of ammonium molybdate was 0.27 g/mL. A carrier of silica was soaked in the mixture, dried in an oven at 120° C. for 12 hrs, and nitrided in the presence of $NH_3$ at 700° C. for one hour to yield a Ni—$Mo_2N$/$SiO_2$ catalyst comprising 15 wt % of nickel and 15 wt % of molybdenum.

EXAMPLE 13

Preparation of a Nickel-Molybdenum/Alumina Catalyst

A carrier of alumina was soaked in a mixed solution of nickel nitrate and ammonium molybdate, dried in an oven at 120° C. for 12 hrs, and reduced in the presence of hydrogen at 700° C. for one hour to yield a Ni—Mo/$Al_2O_3$ catalyst comprising 15 wt % of nickel and 15 wt % of molybdenum.

EXAMPLE 14

Preparation of a Molybdenum Phosphide Catalyst

A mixed solution of ammonium molybdate and diammonium phosphate with a Mo/P atomic ratio of 1:1.2 was prepared. A carrier of titanium dioxide was soaked in the solution, dried at 120° C., and reduced in the presence of hydrogen at 650° C. for 2 hrs to yield a MoP/$TiO_2$ catalyst comprising 10 wt % of molybdenum.

EXAMPLE 15

Preparation of an Iridium-Molybdenum Phosphide Catalyst

A mixed solution of ammonium molybdate, diammonium phosphate, and iridium acid chloride with a Mo/P atomic ratio of 1:1.2 and Mo/Ir weight ratio of 10:1 was prepared. A carrier of titanium dioxide was soaked in the solution, dried at 120° C., and reduced in the presence of hydrogen at 650° C. for 2 hrs to yield an Ir—MoP/$TiO_2$ catalyst comprising 1 wt % of iridium and 10 wt % of molybdenum.

EXAMPLE 16

Experiments of Catalytic Degradation of Starch

To a 200 mL reactor, 1.0 g of a polyhydroxy compound, 0.3 g of a catalyst, and 100 mL of water were added. The reactor was filled in hydrogen and vented three times to remove air. Subsequently, hydrogen pressure in the reactor was increased to 5 MPa, and the temperature therein meanwhile increased to 240° C. After thirty minutes reaction thereafter, the mixture in the reactor was cooled to room temperature and centrifugated to yield a supernatant. The supernatant was analyzed using high performance liquid chromatography (HPLC) with a calcium ion-exchange column and detected using a refractive index detector. The yields of ethylene glycol and hexitols comprising sorbitol and mannitol were calculated. The yields of other liquid products, such as propylene glycol, butantetraol, ethanol, etc., and gas products, such as $CO_2$, $CH_4$, $C_2H_6$, etc., were ignored.

EXAMPLE 17

Following the method described in Example 16, starch was degraded in the presence of a catalyst to yield ethylene glycol. The results are shown in Table 1.

TABLE 1

Conversion of starch to ethylene glycol in the presence of various catalysts

| Catalyst | Yield of ethylene glycol % | Yield of hexitols % | Other products % |
|---|---|---|---|
| Ni—W/AC(5% Ni—18% W) | 56 | 6 | 38 |
| Pt—W/AC(0.5% Pt—75% W) | 51 | 10 | 39 |
| Ni/AC(5% Ni) | 8 | 48 | 44 |
| Pt/AC(0.5% Pt) | 5 | 45 | 50 |
| W/AC(20% W) | 3 | 0 | 97 |
| Ru—$W_2$C/AC(5% Ru—10% W) | 48 | 11 | 41 |
| Ru/AC(5% Ru) | 6 | 10 | 84 |
| $W_2$C/AC(20% W) | 12 | 3 | 85 |
| Ni—$W_2$C/AC(5% Ni—18% W) | 54 | 7 | 39 |
| Ni—$W_2$N/$SiO_2$(15% Ni—15% W) | 43 | 5 | 52 |
| Ni/$SiO_2$(15% Ni) | 5 | 44 | 51 |
| $W_2$N/AC(15% W) | 8 | 4 | 88 |
| Ni—Mo/$Al_2O_3$(15% Ni—15% Mo) | 32 | 5 | 63 |
| Ir—MoP/$TiO_2$(1% Ir—10% Mo) | 38 | 7 | 55 |
| Co—$Mo_2$C/AC(10% Co—20% Mo) | 31 | 4 | 65 |
| Ni—$Mo_2$N/AC(15% Ni—15% Mo) | 36 | 8 | 56 |
| $W_2$C/AC(20% W) + Ru/AC (5% Ru) | 50 | 12 | 38 |
| $Mo_2$N/AC(25% Mo) + Ru/C(5% Ru) | 37 | 11 | 52 |
| $W_2$N/AC(15% W) + Ru/AC(5% Ru) | 45 | 13 | 42 |
| W/AC(20% W) + Raney Ni | 52 | 7 | 41 |

As shown in Table 1, using various metal catalysts of the invention, starch was degraded into ethylene glycol in high yield. The yield of ethylene glycol reached 56% using Ni—W/AC as a catalyst. Mechanical mixing of a first catalyst comprising tungsten and/or molybdenum as an active ingredient and a second catalyst comprising a transition metal of Group 8, 9, or 10 as an active ingredient produced a resultant mixture that retained the ability to degrade starch into ethylene glycol in high yield.

EXAMPLE 18

Following the method of Example 16, sucrose was degraded in the presence of a catalyst to yield ethylene glycol. The results are shown in Table 2.

TABLE 2

Conversion of sucrose to ethylene glycol in the presence of various catalysts

| Catalyst | Yield of ethylene glycol % | Yield of hexitols % | Other products % |
|---|---|---|---|
| Ni—W/AC(5% Ni—18% W) | 43 | 28 | 29 |
| Ni/AC(5% Ni) | 7 | 51 | 42 |
| W/AC(20% W) | 3 | 0 | 97 |
| Ru—W$_2$C/AC(5% Ru—10% W) | 32 | 34 | 34 |
| Ru/AC(5% Ru) | 5 | 10 | 85 |
| W$_2$C/AC(20% W) | 11 | 4 | 85 |
| Ni—W$_2$N/SiO$_2$(15% Ni—15% W) | 45 | 31 | 24 |
| Ni/SiO$_2$(15% Ni) | 6 | 47 | 47 |
| W$_2$N/AC(15% W) | 7 | 3 | 90 |
| Ni—Mo/Al$_2$O$_3$(15% Ni—15% Mo) | 25 | 26 | 49 |
| Ir—MoP/TiO$_2$(1% Ir—10% Mo) | 28 | 24 | 48 |
| Co—Mo$_2$C/AC(10% Co—20% Mo) | 26 | 18 | 56 |
| Ni—Mo$_2$N/AC(15% Ni—15% Mo) | 25 | 34 | 41 |
| W/AC(20% W) + Raney Ni | 46 | 21 | 33 |

As shown in Table 2, using various metal catalysts of the invention, sucrose was degraded into ethylene glycol in high yield. Mechanical mixing of a first catalyst comprising tungsten and/or molybdenum as an active ingredient and a second catalyst comprising a transition metal of Group 8, 9, or 10 as an active ingredient produced a resultant mixture that retained the ability to degrade sucrose into ethylene glycol in high yield.

EXAMPLE 19

Following the method of Example 16, glucose was degraded in the presence of a catalyst to yield ethylene glycol. The results are shown in Table 3.

TABLE 3

Conversion of glucose to ethylene glycol in the presence of various catalysts

| Catalyst | Yield of ethylene glycol % | Yield of hexitols % | Other products % |
|---|---|---|---|
| Ni—W/AC(5% Ni—18% W) | 39 | 35 | 26 |
| Ru—W$_2$C/AC(5% Ru—10% W) | 32 | 41 | 27 |
| Ni—W$_2$N/SiO$_2$(15% Ni—15% W) | 37 | 32 | 31 |
| Ni—Mo/Al$_2$O$_3$(15% Ni—15% Mo) | 23 | 29 | 48 |
| Ir—MoP/TiO$_2$(1% Ir—10% Mo) | 24 | 27 | 49 |
| Co—Mo$_2$C/AC(10% Co—20% Mo) | 25 | 16 | 59 |
| Ni—Mo$_2$N/AC(15% Ni—15% Mo) | 22 | 38 | 40 |
| W/AC(20% W) + Raney Ni | 41 | 26 | 33 |

As shown in Table 3, using various metal catalysts of the invention, glucose is degraded into ethylene glycol in high yield. Mechanical mixing of a first catalyst comprising tungsten and/or molybdenum as an active ingredient and a second catalyst comprising a transition metal of Group 8, 9, or 10 as an active ingredient produced a resultant mixture that retained the ability to degrade glucose into ethylene glycol in high yield.

EXAMPLE 20

Following the method of Example 16, fructose was degraded in the presence of a catalyst to yield ethylene glycol. The results are shown in Table 4.

TABLE 4

Conversion of fructose to ethylene glycol in the presence of various catalysts

| Catalyst | Yield of ethylene glycol % | Yield of hexitols % | Other products % |
|---|---|---|---|
| Ni—W/AC(5% Ni—25% W) | 33 | 31 | 36 |
| Ru—W$_2$C/AC(5% Ru—10% W) | 30 | 34 | 36 |
| Ni—W$_2$N/SiO$_2$(15% Ni—15% W) | 34 | 28 | 38 |
| Ni—Mo/Al$_2$O$_3$(15% Ni—15% Mo) | 21 | 25 | 54 |
| Ni—Mo$_2$N/AC(15% Ni—15% Mo) | 23 | 35 | 42 |

As shown in Table 4, using various metal catalyst of the invention, fructose was degraded into ethylene glycol in high yield.

EXAMPLE 21

Following the method of Example 16, hemicellulose was degraded in the presence of a catalyst to yield ethylene glycol. The results are shown in Table 5.

TABLE 5

Conversion of hemicellulose to ethylene glycol in the presence of various catalysts

| Catalyst | Yield of ethylene glycol % | Yield of hexitols % | Other products % |
|---|---|---|---|
| Ni—W/AC(5% Ni—18% W) | 51 | 8 | 41 |
| Ru—W$_2$C/AC(5% Ru—10% W) | 48 | 11 | 41 |
| Ni—W$_2$N/SiO$_2$(15% Ni—15% W) | 52 | 6 | 42 |
| Ni—Mo/Al$_2$O$_3$(15% Ni—15% Mo) | 36 | 5 | 59 |
| Ni—Mo$_2$N/AC(15% Ni—15% Mo) | 31 | 3 | 66 |

TABLE 5-continued

Conversion of hemicellulose to ethylene glycol in the presence of various catalysts

| Catalyst | Yield of ethylene glycol % | Yield of hexitols % | Other products % |
|---|---|---|---|

As shown in Table 5, using various metal catalysts of the invention, hemicellulose was degraded into ethylene glycol in high yield. The yield generally exceeded 50%.

EXAMPLE 22

This example presents a study of the influence of reaction time on the degradation of polyhydroxy compounds. Following the method of Example 16, various polyhydroxy compounds were catalytically degraded in the presence of Ni—W/AC (5% Ni-25% W) under different reaction times. The results are shown in Table 6.

TABLE 6

Conversion of polyhydroxy compounds to ethylene glycol in the presence of Ni—W/AC as a catalyst under different reaction times

| | Starch | | Glucose | | Sucrose | |
|---|---|---|---|---|---|---|
| Reaction time | Yield of ethylene glycol % | Yield of hexitols % | Yield of ethylene glycol % | Yield of hexitols % | Yield of ethylene glycol % | Yield of hexitols % |
| 10 min | 19 | 4 | 16 | 11 | 16 | 8 |
| 30 min | 56 | 6 | 39 | 35 | 43 | 28 |
| 3 h | 54 | 5 | 37 | 31 | 41 | 24 |
| 5 h | 30 | 3 | 24 | 21 | 27 | 14 |
| 24 h | 15 | 2 | 11 | 10 | 12 | 7 |

As shown in the table, under different reaction times in the presence of Ni—W/AC as a catalyst, the yield of ethylene glycol due to the degradation of polyhydroxy compounds was good. The preferable reaction time was between 30 and 180 min.

EXAMPLE 23

This example presents a study of the influence of reaction temperature on the degradation of polyhydroxy compounds. Following the method of Example 16, various polyhydroxy compounds were catalytically degraded in the presence of Ni—W/AC (5% Ni-25% W) at different reaction temperatures. The results are listed in Table 7.

TABLE 7

Conversion of polyhydroxy compounds to ethylene glycol in the presence of Ni—W/AC as a catalyst at different reaction temperatures

| | Starch | | Glucose | | Sucrose | |
|---|---|---|---|---|---|---|
| Temperature (° C.) | Yield of ethylene glycol % | Yield of hexitols % | Yield of ethylene glycol % | Yield of hexitols % | Yield of ethylene glycol % | Yield of hexitols % |
| 130 | 8 | 4 | 6 | 15 | 7 | 6 |
| 180 | 38 | 3 | 29 | 19 | 31 | 16 |
| 220 | 45 | 4 | 31 | 24 | 33 | 21 |
| 240 | 56 | 6 | 39 | 35 | 43 | 28 |
| 250 | 51 | 8 | 37 | 33 | 40 | 25 |
| 270 | 31 | 5 | 24 | 31 | 24 | 21 |

As shown in the table, at different reaction temperatures in the presence of Ni—W/AC as a catalyst, the yield of ethylene glycol due to the degradation of polyhydroxy compounds was good. The preferable reaction temperature was between 180 and 250° C.

EXAMPLE 24

This example presents a study of the influence of reaction pressure on the degradation of polyhydroxy compounds. Following the method of Example 16, various polyhydroxy compounds were catalytically degraded in the presence of Ni—W/AC (5% Ni-25% W) at different reaction pressures. The results are shown in Table 8.

TABLE 8

Conversion of polyhydroxy compounds to ethylene glycol in the presence of Ni—W/AC as a catalyst at different reaction pressures

| Pressure (MPa) | Starch | | Glucose | | Sucrose | |
| --- | --- | --- | --- | --- | --- | --- |
| | Yield of ethylene glycol % | Yield of hexitols % | Yield of ethylene glycol % | Yield of hexitols % | Yield of ethylene glycol % | Yield of hexitols % |
| 2  | 14 | 4  | 10 | 22 | 11 | 19 |
| 3  | 41 | 6  | 31 | 28 | 37 | 21 |
| 5  | 56 | 6  | 39 | 35 | 43 | 28 |
| 6  | 57 | 7  | 41 | 36 | 44 | 28 |
| 7  | 55 | 9  | 40 | 36 | 42 | 32 |
| 12 | 31 | 21 | 23 | 39 | 21 | 35 |

As shown in the table, at different reaction pressures in the presence of Ni—W/AC as a catalyst, the yield of ethylene glycoldue to the degradation of polyhydroxy compounds was good. The preferable reaction pressure was between 3 and 7 MPa.

EXAMPLE 25

In the invention, in the presence of Ni—W/AC (5% Ni-18% W) as a catalyst and starch or glucose as a raw material, following the method of Example 16, ethylene glycol was produced. China Pat. Appl. No. CN200510008652.0 discloses a method for producing diols and polyols with sorbitol. The differences between the two methods are shown in Table 9.

TABLE 9

Comparison of the method according to the invention and a related art method

| Catalyst | Material | Yield of ethylene glycol % |
| --- | --- | --- |
| Ni—W/AC(5% Ni—18% W) | Starch | 56% |
| Ni—W/AC(5% Ni—18% W) | Glucose | 39% |
| Ni/Ru (Method disclosed in CN200510008652.0) | Starch was hydrolyzed with an enzyme to yield glucose which was hydrotreated to yield sorbitol | 15% |

As shown in the table, the yield of ethylene glycolby following the method of the invention is much higher than that in the related art, and the preparation process is much simpler.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for producing ethylene glycol from a polyhydroxy compound, comprising the steps of:
   a) adding said polyhydroxy compound and water to a reactor,
   b) pressurizing the reactor with hydrogen gas at an initial hydrogen pressure, and
   c) allowing said polyhydroxy compound to react in the presence of a catalyst while stirring the reaction mixture; wherein
   said catalyst comprises a first active ingredient and a second active ingredient;
   said first active ingredient is iron, cobalt, ruthenium, rhodium, palladium, iridium, platinum, or a mixture thereof;
   said second active ingredient is tungsten, a carbide, nitride, phosphide of molybdenum, or a carbide, nitride, phosphide of tungsten; and
   the initial hydrogen pressure in said reactor at room temperature is between 1 and 12 MPa, the reaction temperature between 120 and 300° C., and the reaction time not less than 5 min.

2. The method of claim 1, wherein said polyhydroxy compound is starch, hemicellulose, glucose, sucrose, fructose, fructan, or a mixture thereof.

3. The method of claim 1, wherein the initial hydrogen pressure in said reactor is between 3 and 7 MPa at room temperature, the reaction temperature is between 180 and 250° C., and the reaction time is between 30 and 180 min.

4. The method of claim 1, wherein the weight ratio of said second active ingredient to said first ingredient is between 0.02 and 1600.

5. The method of claim 4, wherein the weight ratio of said second active ingredient to said first ingredient is between 0.3 and 60.

6. The method of claim 1, wherein said first and second active ingredient are supported by a carrier comprising activated carbon, alumina, silica, silicon carbide, zirconia, zinc oxide, titanium dioxide, or a mixture thereof.

7. The method of claim 1, wherein the metal component of said first active ingredient accounts for between 0.05 and 50 wt % of said catalyst.

8. The method of claim 7, wherein the metal component of said first active ingredient accounts for between 1 and 30 wt % of said catalyst.

9. The method of claim 1, wherein the metal component of said second active ingredient accounts for between 1 and 80 wt % of said catalyst.

10. The method of claim 9, wherein the metal component of said second active ingredient accounts for between 10 and 60 wt % of said catalyst.

11. The method of claim 1, wherein said catalyst is not supported and an active ingredient thereof is a skeletal catalyst.

12. The method of claim 11, wherein said catalyst is Raney nickel.

13. The method of claim 1, wherein the weight ratio of said polyhydroxy compound to water is between 1:200 and 1:4.

14. The method of claim 1, wherein the weight ratio of said polyhydroxy compound to said catalyst is between 1:1 and 100:1.

15. The method of claim 1, wherein said reactor is a high-pressure reactor, a fixed bed reactor, or a slurry bed reactor.

16. A method for producing ethylene glycol from a polyhydroxy compound, the method consisting of:
   a) adding said polyhydroxy compound and water to a reactor,
   b) pressurizing the reactor with hydrogen gas at an initial hydrogen pressure, and
   c) allowing said polyhydroxy compound to react in the presence of a catalyst while stirring the reaction mixture;
   wherein:
      said catalyst consists of a first active ingredient and a second active ingredient;
      said first active ingredient is iron, cobalt, nickel, ruthenium, rhodium, palladium, iridium, platinum, or a mixture thereof; and
      said second active ingredient is molybdenum, molybdenum carbide, molybdenum nitride, molybdenum phosphide, tungsten, tungsten carbide, tungsten nitride, tungsten phosphide, or a mixture thereof.

17. The method of claim 16, wherein said first active ingredient is iron, cobalt, ruthenium, rhodium, palladium, iridium, or platinum.

18. The method of claim 16, wherein said second active ingredient is tungsten, tungsten carbide, tungsten nitride, or tungsten phosphide.

19. The method of claim 16, wherein a weight ratio of said second active ingredient to said first ingredient is between 0.3:1 and 60:1.

20. A method for producing ethylene glycol from a polyhydroxy compound, the method consisting of:
   a) adding said polyhydroxy compound and water to a reactor,
   b) pressurizing the reactor with hydrogen gas at an initial hydrogen pressure, and
   c) allowing said polyhydroxy compound to react in the presence of a catalyst while stirring the reaction mixture;
   wherein:
      said catalyst consists of a first active ingredient and a second active ingredient;
      said first active ingredient is ruthenium, rhodium, palladium, iridium, platinum, or a mixture thereof; and
      said second active ingredient is molybdenum carbide, molybdenum nitride, molybdenum phosphide, tungsten carbide, tungsten nitride, tungsten phosphide, or a mixture thereof.

* * * * *